(12) United States Patent
Oba et al.

(10) Patent No.: US 7,449,014 B2
(45) Date of Patent: Nov. 11, 2008

(54) DISPOSABLE WEARING ARTICLE

(75) Inventors: Toru Oba, Kagawa-ken (JP); Takanori Matsuo, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 11/363,217

(22) Filed: Feb. 28, 2006

(65) Prior Publication Data

US 2006/0200109 A1  Sep. 7, 2006

(30) Foreign Application Priority Data

Mar. 4, 2005 (JP) ............................. 2005-060485

(51) Int. Cl.
*A61F 13/20* (2006.01)
(52) U.S. Cl. .................... 604/385.25; 604/385.27; 604/387; 604/391; 604/385.24; 604/385.01; 604/398
(58) Field of Classification Search ............ 604/385.25, 604/385.27, 387, 391, 385.24, 385.01, 398
See application file for complete search history.

(56) References Cited

U.S. PATENT DOCUMENTS

| | | | | |
|---|---|---|---|---|
| 5,055,103 A | * | 10/1991 | Nomura et al. | 604/385.29 |
| 5,188,627 A | * | 2/1993 | Igaue et al. | 604/385.27 |
| 5,836,931 A | * | 11/1998 | Toyoda et al. | 604/385.29 |
| 6,013,065 A | * | 1/2000 | Suzuki et al. | 604/385.27 |
| 6,179,820 B1 | * | 1/2001 | Fernfors | 604/385.27 |
| 6,306,122 B1 | * | 10/2001 | Narawa et al. | 604/385.3 |
| 2004/0133181 A1 | * | 7/2004 | Ishiguro et al. | 604/385.28 |
| 2005/0075618 A1 | * | 4/2005 | Kenmochi et al. | 604/385.27 |

FOREIGN PATENT DOCUMENTS

| | | |
|---|---|---|
| JP | 7-289586 | 11/1995 |
| JP | 2004-236775 | 8/2004 |

* cited by examiner

*Primary Examiner*—T. Zalukaeva
*Assistant Examiner*—Ginger T Chapman
(74) *Attorney, Agent, or Firm*—Lowe Hauptman Ham & Berner, LLP

(57) ABSTRACT

A disposable wearing article is provided with leg elastic elements. The leg elastic elements include first leg elastic elements extending from transversely opposite margins of a front waist region to a front half of a crotch region and second leg elastic elements extending from transversely opposite margins of a rear waist region toward a rear half of the crotch region across a rear half of the crotch region. The first elastic elements extend generally in a transverse direction while the second elastic elements extend in a direction orthogonal to a transverse center line in such a manner that these elastic elements get nearer to a longitudinal center line as these elastic element extend from the rear waist region toward the crotch region.

11 Claims, 8 Drawing Sheets

DISPOSABLE WEARING ARTICLE

BACKGROUND OF THE INVENTION

The present invention relates to a disposable wearing article for absorption and containment of bodily waste.

Conventional disposable wearing articles comprising front and rear waist regions opposed to each other and a crotch region extending between these waist regions. The article includes a plurality of waist elastic elements attached to a longitudinally opposite ends thereof in a contractible manner and a plurality of leg elastic elements attached to transversely opposite sides of the crotch region in a contractible manner. One of such articles is disclosed in Japanese Unexamined Patent Application Publication No. 1995-289586 (hereinafter referred to as "Reference 1"). The front and rear waist regions are overlapped with each other along the transversely opposite sides of the waist regions and these transversely opposite sides are permanently bonded together at a plurality of heat-sealing lines arranged intermittently along the respective transversely opposite sides of these waist regions. Thus, this article is of pants-type or pull-on type having a waist-hole and a pair of leg-holes.

The waist elastic elements are sandwiched between top- and backsheets of the article and bonded to these sheets. The leg elastic elements comprise first elastic elements extending from the side of the front waist region into the crotch region so as to be convex toward a middle zone of the crotch region and second elastic elements extending from the side of the rear waist region into the crotch region so as to be convex toward the middle zone of the crotch region. The first elastic elements comprise transversely opposite lateral segments and intermediate segments extending between these lateral segments across the middle zone of the crotch region. The second elastic elements comprise transversely opposite lateral segments and intermediate segments extending between these lateral segments across the middle zone of the crotch region. The lateral segments of the first and second elastic elements are sandwiched between the top- and backsheets and permanently bonded to these sheets. The intermediate segments of the first and second elastic elements intersect with each other and are sandwiched between the backsheet and the core to be bonded to them. Both the waist elastic elements and the leg elastic elements are stretched at a predetermined ratio for bonding of these elastic elements and relaxed after bonding has been completed.

In the case of the wearing article disclosed in Reference 1, the respective lateral segments of the first elastic elements constituting the leg elastic elements extend in parallel to a longitudinal center line. With a problemsome consequence, even if contractile force of the lateral segments of the first elastic elements may cause the core to contract in the longitudinal direction, such contractile force can not function to press the core against the wearer's skin. In other words, contractile force of the lateral segments of the first elastic elements can not be utilized to maintain the core extending over the front waist region as well as the crotch region in close contact with the wearer's skin. If the core is spaced from the wearer's skin during use of the article, urea discharged on the article may be insufficiently absorbed by the core and leak of urine may occur. In addition, the respective intermediate segments of the first and second leg elastic elements extend across the core which extends in the crotch region and contractile force of these intermediate segments may possibly cause the core to contract in the transverse direction. Consequentially, the core may be formed with a plurality of irregular gathers tending to deteriorate a liquid absorbing function of the core in the crotch region and these gathers may make effective absorption and containment of bodily waste insufficient in the crotch region.

SUMMARY OF THE INVENTION

In view of the problem as has been described above, it is an object of the present invention to provide a disposable wearing article improved so that the crotch region is formed with none of those irregular gathers and contractile force of the first leg elastic elements can be utilized to maintain the core in close contact with the wearer's skin.

According to the present invention, there is provided a disposable wearing article having a longitudinal center line and a transverse center line, the article comprising a backsheet and a liquid-absorbent element placed on the backsheet so as to define front and rear waist regions and a crotch region extending between these waist regions, the article being contoured by longitudinally opposite margins extending in a transverse direction and transversely opposite margins extending in a longitudinal direction, wherein transversely opposite margins of the crotch region are provided with leg elastic elements attached in a contractible manner.

The present invention further comprises the leg elastic elements comprising first elastic elements extending from transversely opposite margins of the front waist region to vicinities of transversely opposite margins of the absorbent element in a front half of the crotch region and second elastic elements extending from the transversely opposite margins of the rear waist region to the front half of the crotch region beyond the transverse center line, wherein the first elastic elements extend generally in the transverse direction while the second elastic elements extend in a direction orthogonal to the transverse direction in such a manner that these elastic elements get nearer to the longitudinal center line as these elastic elements extend from the rear waist region toward the crotch region.

According to another preferred embodiment of the invention, inner ends of the first elastic elements lying in the crotch region extend inward beyond transversely opposite edges of the absorbent element.

According to still another preferred embodiment of the invention, the article includes a pair of barrier sheets lying on the transversely opposite margins thereof.

In the disposable wearing article according to this invention, the first leg elastic elements extend generally in the transverse direction. Such a feature ensures that the contractile force of the first elastic elements stretched generally in the transverse direction during use of the article functions to put the absorbent element extending over the front waist region and the front half of the crotch region in close contact with the wearer's body. In this manner, it is possible to put the absorbent element in close contact with the wearer's body under the contractile force of the first elastic elements. Consequentially, the article ensures that urine discharged during use of the article is reliably absorbed and contained to prevent urine discharged during use of the article from leaking. The second leg elastic elements extend in the direction orthogonal to the transverse direction so as to get nearer to the longitudinal center line. Such a feature ensures that the contractile force of the second elastic elements functions to pull the rear waist region and the rear half of the crotch region up toward the longitudinally opposite margins of the article and thereby to prevent the article from slipping down from the position at which the article should be held.

DETAILED DESCRIPTION OF THE PREFERRED EMBODIMENTS

Figure 1:
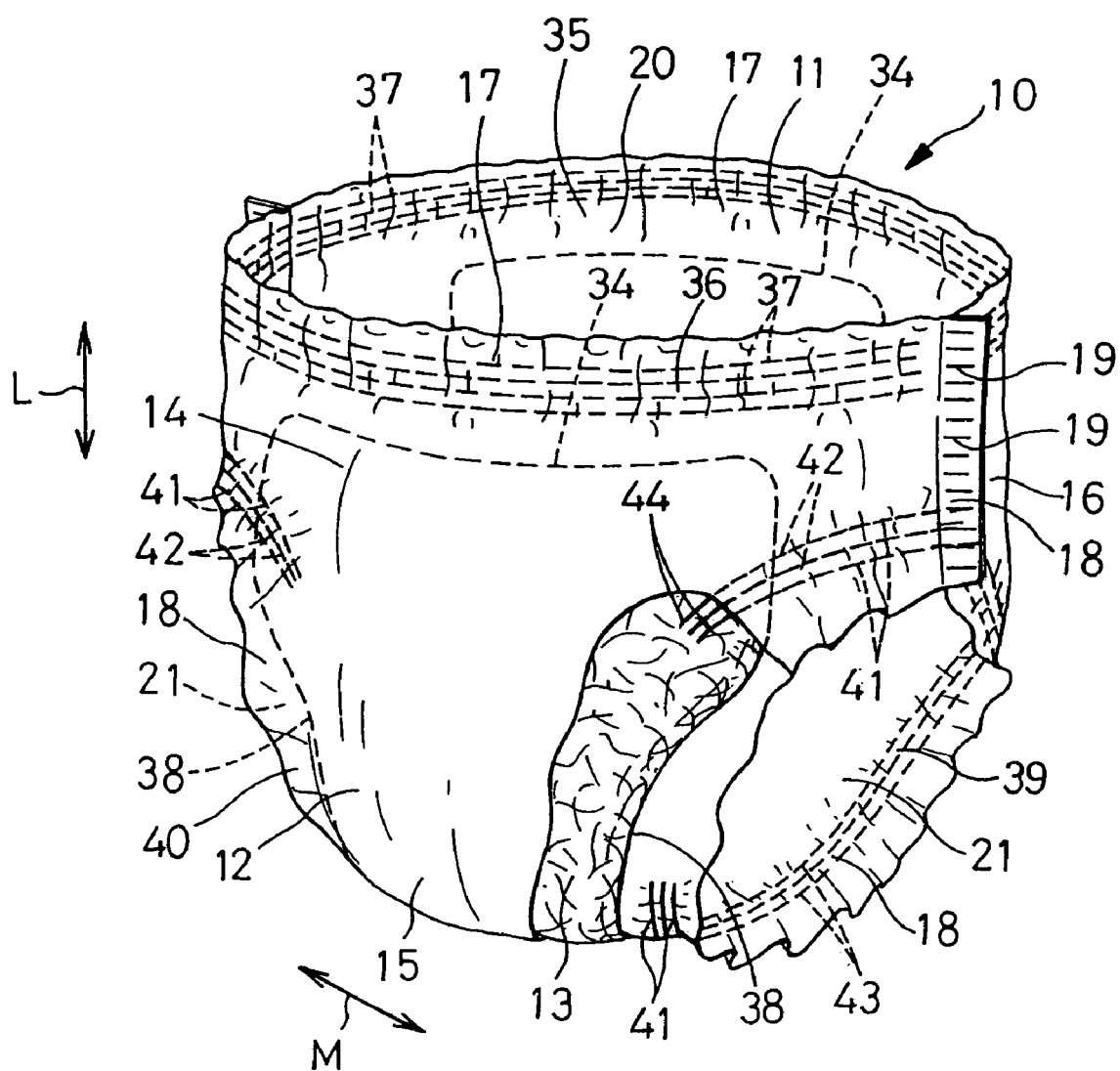
FIG. 1 is a partially cutaway perspective view showing a first embodiment of a disposable wearing article according to the present invention.

Details of a disposable wearing article according to the present invention will be more fully understood from the description given hereunder with reference to the accompanying drawings.

Referring now to FIGS. 1-4 showing a disposable wearing article as a first embodiment of the present invention, the article has longitudinal and transverse directions indicated by arrows L and M, respectively.

The article 10 comprises a liquid-pervious topsheet 11 facing the wearer's skin, a liquid-impervious backsheet 12 facing away from the wearer's skin and a liquid-absorbent element 13 interposed between these sheets 11, 12. The article 10 is configured to define front and rear waist regions 14, 16 opposed to each other and a crotch region 15 extending between these waist regions 14, 16. The article 10 has longitudinally opposite margins 17 of the front and rear waist regions 14, 16, respectively, extending in the transverse direction and transversely opposite margins 18 of the front and rear waist regions 14, 16, respectively, extending in the longitudinal direction. The absorbent element 13 extends over the front waist region 14, the rear waist regions 16 and the crotch region 15 except the longitudinally opposed margins 17 and the transversely opposite margins 18. Transversely opposite margins 18a of the front waist region 14 and transversely opposite margins 18b of the rear waist region 16 are overlapped and permanently bonded together at a plurality of heat sealing lines 19 arranged intermittently in the longitudinal direction along the respective transversely opposite margins 18a, 18b. As will be apparent from FIGS. 1 and 2, the article 10 is of pants-type or pull-on type having a waist-hole 20 and a pair of leg-holes 21.

As a stock material for the topsheet 11, a hydrophilic fibrous nonwoven fabric is used. As a stock material for the backsheet 12, a hydrophobic fibrous nonwoven fabric is used. The element 13 is a mixture of particulate or fibrous super-absorbent polymers and fluff pulp or a mixture of particulate or fibrous super-absorbent polymers, fluff pulp and thermoplastic synthetic resin fibers, in any case, compressed to a given thickness. The element 13 is entirely wrapped with a tissue paper (not shown) in order to prevent the element 13 from getting out of its desired shape and/or to prevent the polymers from falling off. The element 13 is bonded to respective inner surfaces of the top- and backsheets 11, 12 through the intermediary of the tissue paper. The polymers may be selected from the group consisting of starch-based polymers, cellulose-based polymers and synthetic polymers.

Figure 2:
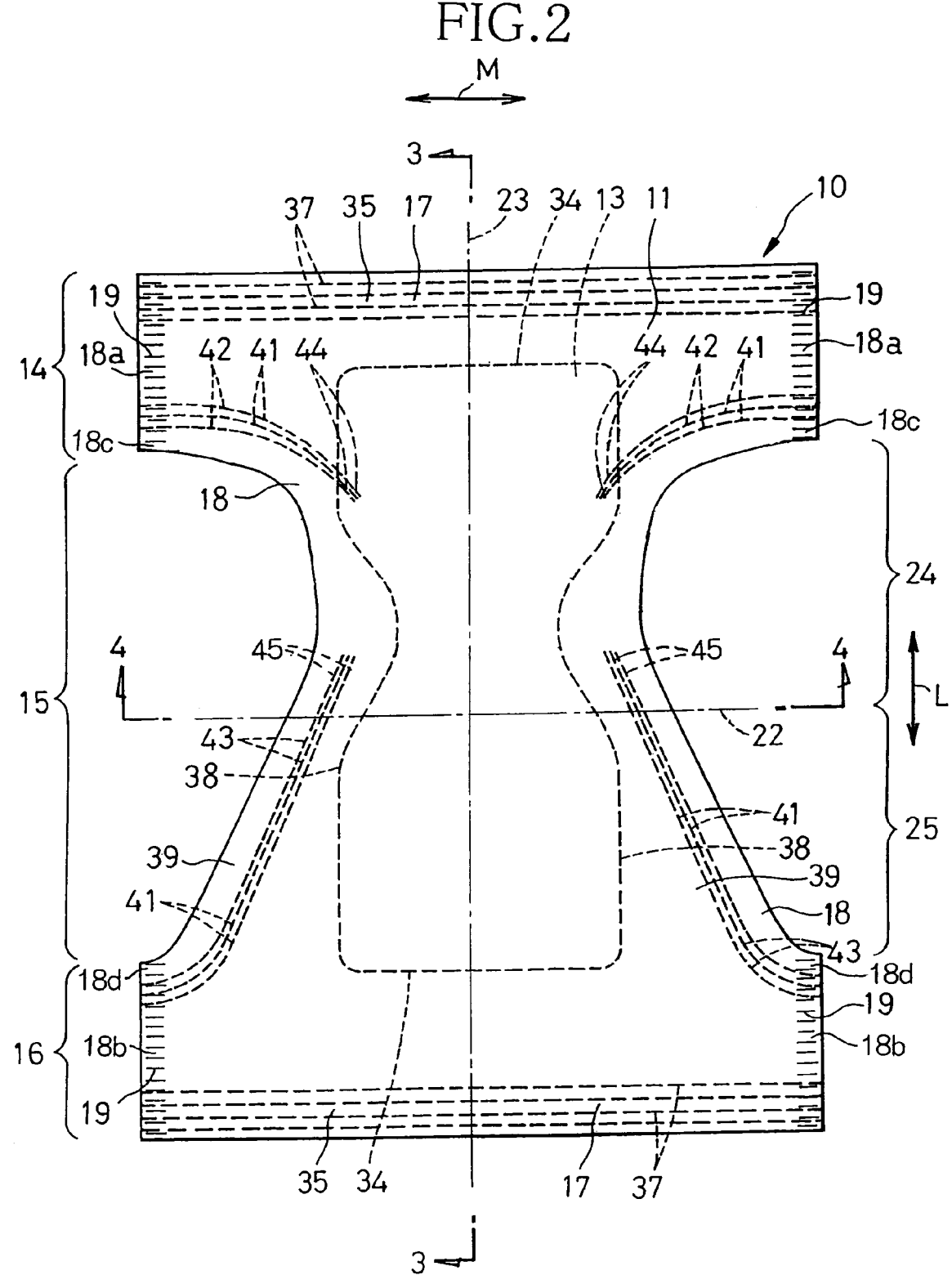
FIG. 2 is a developed plan view showing the article of FIG. 1 with a front and rear waist regions disconnected from each other.
Figure 3:
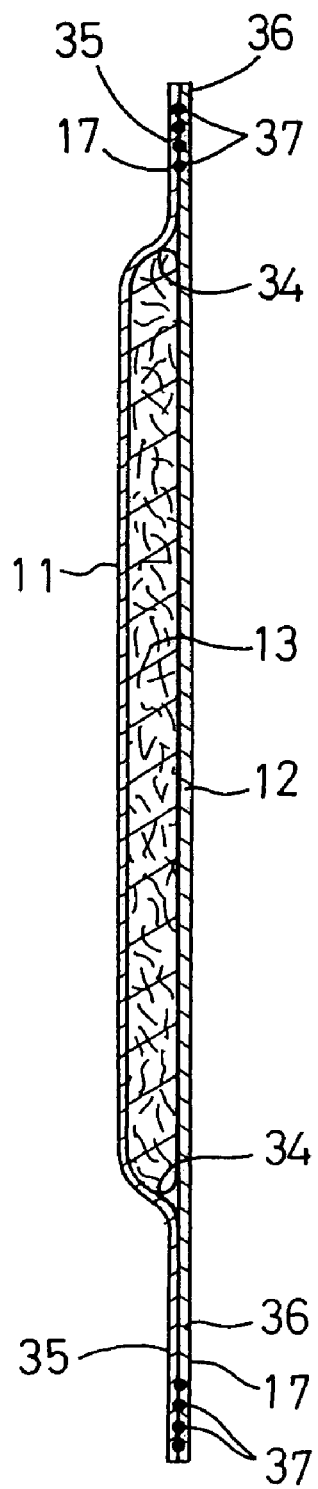
FIG. 3 is a sectional view taken along section line 3-3 in FIG. 2.
Figure 4:
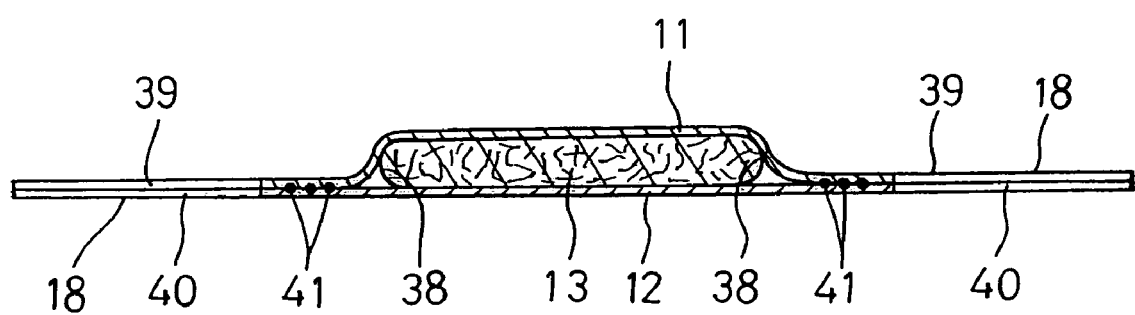
FIG. 4 is a sectional view taken along section line 4-4 in FIG. 2.
Figure 5:
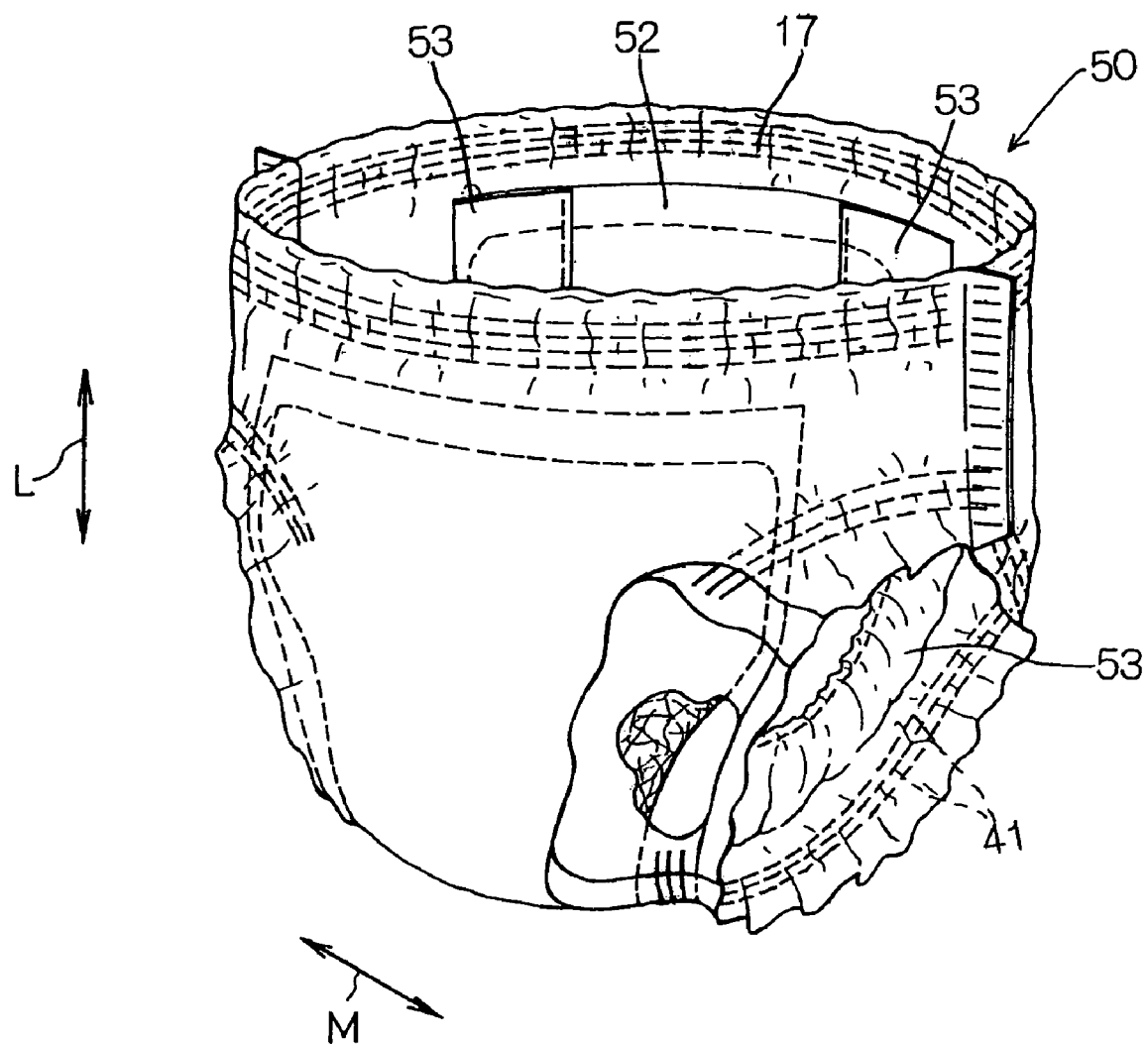
FIG. 5 is a partially cutaway perspective view showing second embodiment of the disposable wearing article according to the present invention.
Figure 6:
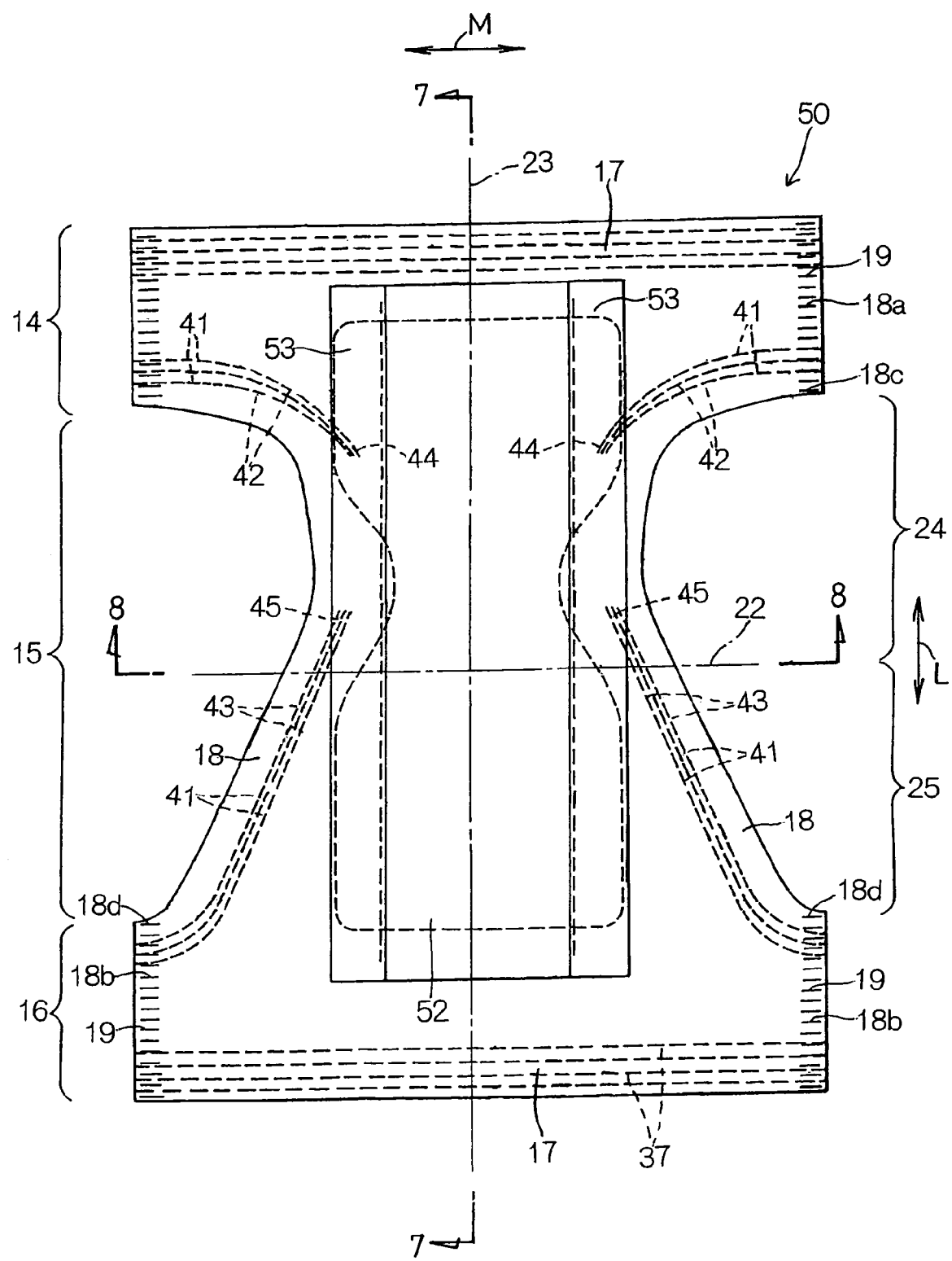
FIG. 6 is a developed plan view showing the article of FIG. 5 with the front and rear waist regions disconnected from each other.
Figure 7:
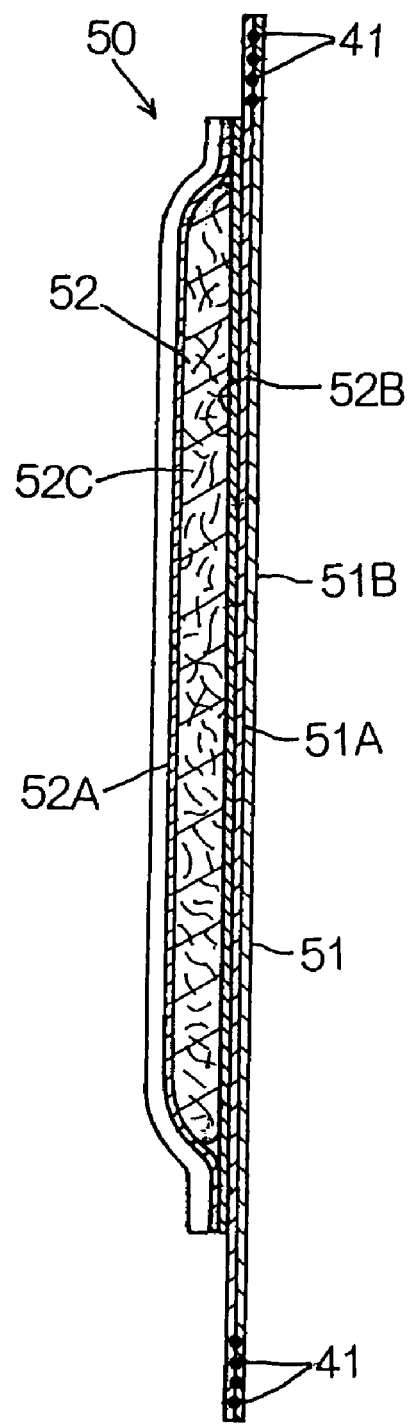
FIG. 7 is a sectional view taken along section line 7-7 in FIG. 6.
Figure 8:
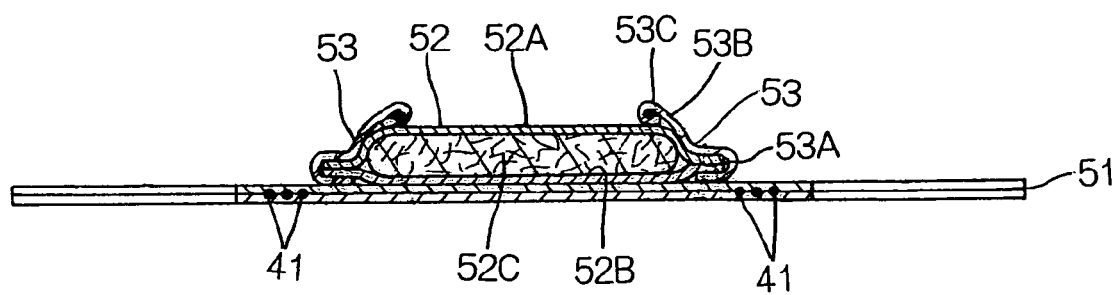
FIG. 8 is a sectional view taken along section line 8-8 in FIG. 6.

In FIG. 2, a transverse center line 22 (chain line) extends in the transverse direction to bisect a longitudinal dimension of the article 10 and a longitudinal center line 23 (chain line) extends in the longitudinal direction to bisect a transverse dimension of the article 10. The crotch region 15 is divided into a front half 24 extending between the front waist region 14 and the transverse center line 22 and a rear half 25 extending between the transverse center line 22 and the rear waist region 16.

The crotch region 15 has its side edges 18c concavely curved toward the longitudinal center line 23 so that a width of the crotch region 15 is gradually narrowed from the rear waist region 16 toward the front waist region 14 and then the width of the crotch region 15 is gradually widened from a zone slightly beyond the transverse center line 22 toward the front waist region 14. Thus, the article is configured to a generally hourglass like planer shape.

The longitudinally opposite margins 17 are defined by longitudinally opposite margins 35, 36 of the top- and backsheets 11, 12, respectively, extending outward in the longitudinal direction beyond longitudinally opposite ends 34 of the absorbent element 13. Along these margins 17, the margins 35, 36 of the top- and backsheets 11, 12 are overlapped with each other and have permanently bonded together. A plurality of string-like waist elastic elements 37 extending in the transverse direction along the waist-hole 20 are secured to the respective margins 17 in a contractible manner. Specifically, these waist elastic elements 37 are sandwiched between the top- and backsheets 11, 12 and bonded to respective inner surfaces of these sheets 11, 12. The waist elastic elements 37 are stretched at a given ratio in the course of being bonded to the sheets 11, 12 and relaxed upon completion of bonding.

The transversely opposite margins 18 are defined by transversely opposite margins 39, 40 of the top- and backsheets 11, 12 extending outward in the transverse direction beyond transversely opposite edges 38 of the absorbent element 13. Along these margins 18, the margins 39, 40 of the top- and backsheets 11, 12 are overlapped with each other and have permanently bonded together. A plurality of string-like leg elastic elements 41 extending generally along curves of the respective leg-holes 21 are secured to the respective margins 18 in a contractible manner. Specifically, the leg elastic elements 41 are sandwiched between the top- and backsheets 11, 12 and bonded to respective inner surfaces of these sheets 11, 12. The leg elastic elements 41 are stretched at a given ratio in the course of being secured to the sheets 11, 12 and relaxed upon completion of securing.

The leg elastic elements 41 comprise first leg elastic elements 42 extending from vicinities of inner portions 18c of the transversely opposite margins 18a of the front waist region 14 to the front half 24 of the crotch region 15 and second leg elastic elements 43 extending from vicinities of inner portions 18d of the transversely opposite margins 18 of the rear waist region 16 to the front half 24 of the crotch region 15 beyond the transverse center line 22. The first elastic elements 42 extending with a convexly curve toward the margin 17 of the front waist region 14, however, may extend generally in parallel to the transverse center line 22. The inner ends 44 of the first elastic elements 42 lying in the front half 24 extend inward beyond the transversely opposite edges 38 of the absorbent element 13. The second elastic elements 43 extend in a direction orthogonal to the transverse center line 22 in such a manner that these elastic elements 43 get nearer to the longitudinal center line 23 as these elastic elements extend from the rear waist region 16 toward the crotch region 15. The first and second elastic elements 42, 43 are spaced apart from each other in longitudinally middle zones of the front half 24 of the crotch region 15.

To put the article 10 on the wearer's body, after the wearer's legs have been inserted through the waist-hole 20 into the respective leg-holes 21, the article 10 is pulled up to the wearer's waist. During use of the article 10, on one hand, the first elastic elements 42 are stretched generally in the transverse direction and the contractile force of these first elastic elements 42 functions to hold the absorbent element 13 extending over the front waist region 14 and the front half 24 of the crotch region 15 in close contact with the wearer's skin. During use of the article 10, on the other hand, the second elastic elements 43 are stretched in the direction orthogonal to the transverse center line 22, mere strictly, the contractile of these second elastic elements 43 functions to pull the rear half 25 of the crotch region 15 and the rear waist region 16 up toward the longitudinally opposite margins 17 of the article 10.

The contractile force of the first elastic elements 42 effectively functions to hold the absorbent element 13 extending over the front waist region 14 and the front half 24 of the crotch region 15 in close contact with the wearer's skin during use of the article 10, as has been described above. Furthermore, the article 10 ensures that the absorbent element 13 reliably absorbs and contains urine discharged during use of the article 10 and thereby prevents urine discharged during use of the article 10 from leaking. During use of the article 10, the contractile force of the second elastic elements 43 functions to pull the rear half 25 of the crotch region 15 and the rear waist region 16 up toward the longitudinally opposite margins 17 and thereby to prevent the article 10 from slipping down off the position at which the article 10 should be held. The feature that none of the first and second elastic elements 42, 43 is present in the longitudinally middle zones of the first front half 24 of the crotch region 15 is effective to eliminate a possibility that the absorbent element 13 might be formed with a plurality of irregular gathers due to the contractile force of the elastic elements 42, 43 as has often occurred in the conventional articles having these elastic elements continuously extending across the absorbent element 13. Without any anxiety that the liquid absorbing function of the absorbent element 13 extending over the crotch region 15 might be deteriorated, the article 10 ensures that bodily waste can be satisfactorily absorbed and contained by the absorbent element 13 in the crotch region 15.

Referring to FIGS. 5-8 showing a disposable wearing article 50 as a second embodiment of the present invention, the article 50 is principally different from the article 10 in the first embodiment of the invention in that the article 10 basically comprises the liquid-pervious topsheet 11, the liquid-impervious backsheet 12 and the liquid-absorbent element 13, whereas the article 50 comprise a liquid-impervious backsheet 51 and a liquid-absorbent panel 52 laid on the inner surface of the first backsheet 51 wherein the backsheet 51 comprises an inner sheet 51A and an outer sheet 51B and the absorbent panel 52 comprises a liquid-pervious topsheet 52A, a liquid-impervious second backsheet 52B and a liquid-second absorbent element 52C.

The waist and leg elastic elements 17, 41 are secured between the inner and outer sheets 51A, 51B of the backsheet 51. The inner and outer sheets 51A, 51B are from a composite nonwoven fabric of hydrophobic fibrous nonwoven fabrics laminated together. In the absorbent panel 52, the second backsheet 52B is fixed to the inner surface of the backsheet 51. The absorbent panel 52 comprises a pair of leak-barrier sheets 53. The leak-barrier sheets 53 are spaced apart from and opposed to each other in the transverse direction and attached to the transversely opposite margins of the absorbent panel 52. The leak-barrier sheets 53 comprise proximal edges 53A fixed to the transversely opposite margins of the absorbent panel 52, distal edges 53B elasticized by elastic element 53C secured to uppermost edges of the distal edges 53B. As a stock material for the leak-barrier sheet 53, a hydrophobic fibrous nonwoven fabric is used.

Other structure of the article 50 is substantially similar to the article 10. Components of the article 50 similar to those previously described have the same reference numeral and the same components and arrangements are not repeatedly described.

The entire discloses of Japanese Patent Application No. 2005-60485 filed on Mar. 4, 2005 including specification, drawings and abstract are herein incorporated by reference in its entirety.

What is claimed is:

1. A disposable wearing article having a longitudinal center line extending in a longitudinal direction of said article and a transverse center line extending in a transverse direction of said article, said article comprising:

a backsheet and a liquid-absorbent element placed on said backsheet, front and rear waist regions and a crotch region extending between said waist regions, longitudinally opposite margins extending in the transverse direction and transversely opposite margins extending in the longitudinal direction, and contractible leg elastic elements provided along the transversely opposite margins in said crotch region, said leg elastic elements comprising:

first elastic elements extending from the transversely opposite margins in said front waist region to vicinities of transversely opposite edges of said absorbent element in a front half of said crotch region, and second elastic elements extending from said transversely opposite margins in said rear waist region toward said front half of said crotch region and beyond said transverse center line, wherein said first elastic elements extend generally in said transverse direction while said second elastic elements extend in a direction orthogonal to said transverse direction in such a manner that said second elastic elements get nearer to said longitudinal center line as said second elastic elements extend from said rear waist region toward the front half of said crotch region, wherein the first elastic elements terminate at their respective inner ends in the vicinities of the transversely opposite edges of said absorbent element in the front half of said crotch region, and said inner ends of said first elastic elements underlie said absorbent element, wherein the second elastic elements terminate, without crossing any of the first elastic elements, at their respective inner ends in the crotch region, and said inner ends of said second elastic elements do not underlie said absorbent element, and wherein the inner ends of the first elastic elements are closer to the longitudinal center line than the inner ends of the second elastic elements;

wherein said article further comprises a pair of barrier sheets lying on said transversely opposite edges of said absorbent element, and wherein said barrier sheets comprise proximal edges and elasticized edges; and wherein the proximal edges of said barrier sheets cross the first and second elastic elements in vicinities of the inner ends of the first and second elastic elements and connect said inner ends.

2. The article according to claim 1, wherein said first elastic elements lying in said crotch region extend in the transverse direction inward beyond the respective transversely opposite edges of said absorbent element and terminate at their respective inner ends which are located, in the transverse direction, between the transversely opposite edges of said absorbent element.

3. The article according to claim 1, wherein each of said first elastic elements extends inwardly in the transverse direction from one of the transversely opposite margins of said article and terminate at their respective inner ends in the vicinity of an adjacent one of said transversely opposite edges of said absorbent element, without extending all the way to the other of said transversely opposite margins of said article.

4. The article according to claim 3, wherein the first elastic elements, which extend inwardly in the transverse direction from the same one of the transversely opposite margins of said article, converge towards each other as they extend toward the adjacent one of said transversely opposite edges of said absorbent element.

5. The article according to claim 3, wherein each of the inner ends of the second elastic elements is located between one of the transversely opposite margins of the article and an adjacent one of the transversely opposite edges of said absorbent element so that the transversely opposite edges of said absorbent element are located, in the transverse direction, between the inner ends of the second elastic elements.

6. The article according to claim 3, wherein the inner ends of the first elastic elements and the inner ends of the second elastic elements are spaced in the longitudinal direction from each other to define therebetween an elastic-free zone of the crotch region.

7. The article according to claim 1, wherein an entire length of each of said first elastic elements is shorter than a transverse dimension of said article as measured between the transversely opposite margins thereof in the front waist region.

8. The article according to claim 1, wherein each of said first elastic elements crosses only one of the transversely opposite edges of said absorbent element.

9. The article according to claim 1, wherein
a contractile force of the first elastic elements, when stretched in use, is primarily oriented in the transverse direction for holding the absorbent element extending over the front waist region and the front half of the crotch region in close contact with a wearer's skin; and
a contractile force of the second elastic elements, when stretched in use, is primarily oriented in the direction orthogonal to said transverse direction for pulling a rear half of the crotch region and the rear waist region up toward the longitudinally opposite margins of the article.

10. A disposable wearing article having a longitudinal center line extending in a longitudinal direction of said article and a transverse center line extending in a transverse direction of said article, said article comprising:
a backsheet and a liquid-absorbent element placed on said backsheet,
front and rear waist regions and a crotch region extending between said waist regions,
longitudinally opposite margins extending in the transverse direction and transversely opposite margins extending in the longitudinal direction, and
contractible leg elastic elements provided along the transversely opposite margins in said crotch region,
said leg elastic elements comprising:
first elastic elements extending from the transversely opposite margins in said front waist region to vicinities of transversely opposite edges of said absorbent element in a front half of said crotch region, and
second elastic elements extending from said transversely opposite margins in said rear waist region toward said front half of said crotch region and beyond said transverse center line,
wherein said first elastic elements extend generally in said transverse direction while said second elastic elements extend in a direction orthogonal to said transverse direction in such a manner that said second elastic elements get nearer to said longitudinal center line as said second elastic elements extend from said rear waist region toward the front half of said crotch region,
wherein the first elastic elements terminate at their respective inner ends in the vicinities of the transversely opposite edges of said absorbent element in the front half of said crotch region, and said inner ends of said first elastic elements underlie said absorbent element,
wherein the second elastic elements terminate, without crossing any of the first elastic elements, at their respective inner ends in the crotch region, and said inner ends of said second elastic elements do not underlie said absorbent element, and
wherein the inner ends of the first elastic elements are closer to the longitudinal center line than the inner ends of the second elastic elements; and
wherein each of said second elastic elements includes a straight section extending from a vicinity of the respective one of the transversely opposite margins in the rear waist region toward the front half of said crotch region and beyond the transverse center line.

11. The article according to claim 10, wherein said article further comprises:
a pair of barrier sheets lying on said transversely opposite edges of said absorbent element, and wherein said barrier sheets comprise proximal edges and elasticized edges;
wherein the proximal edges of said barrier sheets cross the first and second elastic elements in vicinities of the inner ends of the first and second elastic elements.

* * * * *